United States Patent [19]

Goldring

[11] Patent Number: 4,925,544
[45] Date of Patent: May 15, 1990

[54] ELECTROCHEMICAL SENSOR WITH SOLID PHASE ELECTROLYTE

[75] Inventor: Lionel S. Goldring, Woodbridge, Conn.

[73] Assignee: National Research Development Corporation, London, England

[21] Appl. No.: 303,653
[22] PCT Filed: May 13, 1988
[86] PCT No.: PCT/GB88/00377
    § 371 Date: Feb. 23, 1989
    § 102(e) Date: Feb. 23, 1989
[87] PCT Pub. No.: WO88/08975
    PCT Pub. Date: Nov. 17, 1988

Related U.S. Application Data

[63] Continuation-in-part of Ser. No. 49,902, May 15, 1987, abandoned.

[51] Int. Cl.[5] .................................... G01N 27/26
[52] U.S. Cl. .................................. 204/421; 204/414; 204/415; 204/422; 204/431; 429/30; 429/33; 429/104; 429/192; 324/439; 128/635
[58] Field of Search ............... 204/1 P, 414, 415, 421, 204/422, 431; 128/635; 429/30, 33, 104, 192; 324/438, 439

[56] References Cited

U.S. PATENT DOCUMENTS 4,076,596 2/1978 Connery et al. .................. 204/421
4,587,101 5/1986 Marsoner et al. ................ 428/690
4,728,588 3/1988 Noding et al. .................... 429/192
4,818,361 4/1989 Burgess et al. .................. 204/415

FOREIGN PATENT DOCUMENTS 2054869 2/1981 United Kingdom .
2124387 2/1984 United Kingdom .

OTHER PUBLICATIONS

Pace et al., "Transducers '85", International Conference on Solid State Sensors and Actuators, Digest of Technical Papers, 9-85, IEEE (U.S.), pp. 406-408.
Hardy et al., "Preparation and Electrical Response of Solid Polymer Electrolytes with only One Mobile Species", Chem. Abstracts, vol. 103, 1985, p. 593, #15009d.
Sadaoka et al., "A Humidity Sensor Using Alkali Salt-Polyethylene Oxide Hybrid Film", Chem. Abstracts, vol. 104, 1986, (Columbus, OH, U.S.), p. 413, Abstract #198926p.

Primary Examiner—John F. Niebling
Assistant Examiner—Kathryn Gorgos
Attorney, Agent, or Firm—Howard F. Mandelbaum

[57] ABSTRACT

An electrochemical sensor comprising an electrolyte and an analyte separated by a selectively permeable membrane preferably characterized in that the electrolyte is an electrically conductive solid comprising a homogeneous dispersion of a polymeric matrix phase and an electrically conductive salt and substantially free of water. Preferably the polymeric matrix phase is plasticized, the plasticizer forming a continuous phase in which the conductive salt is dissolved. The sensor is used, for example, for sensing and measuring gases especially in transcutaneous measurement of blood gases.

14 Claims, 3 Drawing Sheets

ELECTROCHEMICAL SENSOR WITH SOLID PHASE ELECTROLYTE

This is a continuation-in-part of application Ser. No. 07/049,902, filed May 15, 1987, now abandoned.

BACKGROUND OF THE INVENTION

This invention relates to electrochemical sensing devices utilizing membranes to separate the electrolyte needed by the device from the medium containing the analyte of interest. More specifically, it relates to: (1) gas sensing devices wherein the membrane is utilized to separate the electrolyte from a liquid containing the gas being analyzed, (2) gas sensing devices wherein the membrane is utilized to separate the electrolyte from a gas phase, and (3) ion sensing devices wherein a selectively permeable membrane separates the liquid electrolyte utilized by the device from the analysis solution, which contains an analyte able to diffuse freely through the membrane.

Included in gas sensing devices wherein the membrane is utilized to separate the electrolyte from a liquid containing the gas being analyzed are the sensors utilized for transcutaneous blood gas monitoring, for clinical laboratory analysis of blood gases, and for laboratory and field measurement of gases such as ammonia, carbon dioxide, oxygen and chlorine. Also included in this category are intravascular (catheter) electrodes with proximal or remote reference electrodes for measuring oxygen or carbon dioxide.

Gas sensing devices wherein the membrane is utilized to separate the electrolyte from a gas phase include electrochemical sensor utilized for measuring gases such as oxygen, carbon dioxide, chlorine, or ammonia in flowing gas streams. Such devices are currently utilized for verifying the oxygen content of gas mixtures used for respiratory therapy.

Ion sensing devices wherein a selectively permeable membrane separates the liquid electrolyte utilized by the device from the analysis solution which contains an analyte able to diffuse freely through the membrane, include, specifically, intravascular electrodes for measuring blood pH, sodium, potassium and glucose.

The invention consists of a method and apparatus to simplify the process of changing the membrane and the electrolyte needed by the electrochemical sensing device. While it is believed that the major value will be with gas sensing devices, the invention can be used with any of the electrochemical devices described above which use replaceable membranes.

Basic to the operation of electrochemical sensors is the presence of an electrolyte, an ionically conducting medium, contacting both the anode and the cathode. In voltammetric oxygen sensors of the Clark type or potentiometric carbon dioxide sensors of the Stow-Severinghaus type or other gas sensors of the types disclosed by Ross and Riseman, this electrolyte is an aqueous solution, sometimes modified by other water-compatible solvents such as ethylene glycol or propylene glycol or glycerol. At times, these other solvents may make up the bulk of the electrolyte solution and the water content may vary from traces to only a few percent.

The membrane in these devices may serve several functions. It can be utilized to prevent evaporation of the electrolyte solvent or to prevent fouling of the electrodes. It can prevent contamination of the electrolyte solution or changes in the solution concentration. It can be selectively permeable, allowing only gases to enter for analysis, or it may allow ions and not proteins to reach the sensing electrodes. It can be a diffusion barrier and provide most of the concentration gradient between the medium being analyzed and the electrode where the analyte is being consumed. It can control the thickness of the electrolyte layer and, under some conditions, control the sensitivity of microelectrodes.

The output stability, i.e., the ability to maintain a reproducible output signal for periods ranging from hours to days when the sensor is exposed to a reproducible gas composition, in both voltammetric and potentiometric sensors, is dependent upon the maintenance of a constant composition in this electrolyte, although the reason for this is different in the two types of sensors.

In voltammetric sensors, e.g., oxygen, stability is dependent upon maintaining the constancy of the diffusional pathways to the cathode. This means that both the geometry of the diffusion layer and any of its properties which affect transport, such as solubility and diffusion coefficient, should remain constant; the response of an oxygen sensor is relatively insensitive to the absolute concentration of any of the ions. With potentiometric sensors, on the other hand, the concentration of one or more of the ions is critically important; for carbon dioxide sensors, a common stability specification requires that concentration changes be limited to less than one percent per hour.

While many factors may have a significant effect upon electrolyte properties, an important one is the diffusion of water vapor through the membrane. This directly affects the concentration of electrolytes, so affecting the readings of potentiometric gas sensing electrodes, and for electrolytes with a low water content, changes may have a strong effect upon the diffusional properties of the electrolyte and so affect voltammetric sensors. Although membranes are typically made from rather hydrophobic polymers, good transient response and a number of engineering considerations have limited the number of satisfactory materials to a small number with intermediate transport properties for oxygen and carbon dioxide and concomitantly, for water vapor.

The need for good transient behavior limits the thickness of the electrolyte layer between the membrane and the sensing electrode. For many electrode configurations, such as transcutaneous devices and intravascular devices, it has heretofore proven impossible to provide a large electrolyte reservoir, and, therefore, the electrolyte has had to be replenished at regular intervals.

Historically, membrane-based electrochemical sensing devices have been prepared for use by placing a small volume of electrolyte so that it is contained between the surface of the structure which contains the electrodes and the membrane which separates the sensor and its electrolyte from the medium being measured. The membrane may be fixed in position by a variety of means, ranging from a rubber band or O-ring to a structure which holds the membrane and which can be fastened to the sensor by screw threads, an interference fit, or an over center, snap-like device. Mechanical aids may be used to facilitate assembly.

With electrolytes used heretofore, the user should add a small volume, usually less than a milliliter and often a drop or less, of the electrolyte to the electrode face or the membrane surface, and this usually requires a fresh membrane because the previous application stretched the membrane enough so that reapplication produces a loose fit. There are several other reasons why membranes have to be replaced at regular intervals—mechanical damage, membrane fouling, the need to polish the electrode surface (in the case of oxygen sensors), and electrolyte evaporation. While changing a membrane is not a difficult operation, it is not only an inconvenience but a continuing potential source of operational errors, and in the clinical environment, especially, any simplification has value.

SUMMARY OF THE INVENTION

In order to overcome at least some of the problems of prior art (electrochemical sensors which use fluid phase electrolytes), the present invention teaches the use and construction of an electrochemical sensor having an electrode, an electrolytic solution in a substantially solid phase at ambient temperatures in electrical contact with said electrode, and a selectively permeable membrane in contact with said electrolytic solution for selectively passing an analyte into said electrolytic solution. More specifically, the invention includes an electrochemical sensor wherein the electrolyte is an electrically conductive solid comprising a homogeneous dispersion of a polymeric matrix phase and an electrically conductive salt. Very desirably, the polymeric matrix phase is plasticized, the platicizer forming a continuous phase in which the conductive salt is dissolved. The preferred polymer is a polyvinyl alcohol and the preferred plasticizer therefor is a polyhydric alcohol or mixture thereof. What is novel and inventive herein lies at least partly in the use in an electrochemical sensing device as defined above of a solid phase electrolyte which is substantially free of water, thereby avoiding variability in the sensor through gradual evaporation of water during use of the sensor. Moreover, the selectively permeable membrane can be replaced easily. In at least the best embodiments of the invention, a good transient response is obtainable, and therefore, the problem of electrolyte replenishment is also overcome.

The invention further includes a method of making an electrochemical sensor of the invention, comprising:

(1) combining, in any order, ingredients including a polymer and an electrically conductive salt (and preferably also a plasticizer and a volatile solvent for said polymer and plasticizer, to form a homogeneous mixture containing the polymer as a matrix phase and when a plasticizer is included a continuous phase thereof in which the conductive salt is dissolved, (2) forming said mixture into a thin film, (3) affixing said film to a membrane, (4) mounting said membrane adjacent said electrode and (5) when said ingredients include a volatile solvent, before or after step (3) drying said film to evaporate substantially all said volatile solvent.

DESCRIPTION OF THE PREFERRED EMBODIMENTS

It is the purpose of this invention to describe a series of solid polymer based electrolyte systems which will eliminate many of the problems associated with the limited life of the electrolyte and provide a system for renewing the electrolyte without the need to handle a separate liquid. This can be done in two ways: (1) by utilizing a solid polymer based electrolyte which is adherent to the membrane; and (2) by preparing a solid polymer based electrolyte which can be handled without a supporting membrane. It can be applied to an electrode in a fashion previously known, utilizing a membrane-handling structure such as a NovaDisk membrane attachment device manufactured by Novametrix Medical Systems, Inc., Wallingford, CT 06492 and more fully described in U.S. Pat. No. 4,280,505 to Dali et al.

There are at least four types of polymer-based systems which can be used to formulate solid polymer based electrolytes for electrochemical sensing devices. These may be described as follows:

(1) Polymer-gelled electrolyte system, wherein well known standard electrolytes bases upon water, glycols, etc. can be converted into semi-rigid solids by using certain water-soluble polymeric gelling agents.

(2) Polymer-plasticiser system based upon plasticisers with high dielectric constants which can be utilized with compatible polymers to produce solid polymer electrolytes usable with intravascular and transcutaneous sensors. These do not have the high resistance characteristc of previously known systems, such as those based upon PVC and other polymers with relatively low polarity; therefore, they make effective solid electrolytes for use with oxygen sensors.

(3) Polymer-salt complex system based on polyethylene oxide and derivatives, with sufficiently high conductivity to be effective solid polymer electrolytes for oxygen sensors. Their successful utilization in sensors is dependent upon modifications which will provide high rates of diffusion and the incorporation of anions which will support anode reactions and stabilise reference electrodes for voltametric sensors and potentiometric sensors, respectively.

(4) Ion exchange membrane system. A solvent-soluble, cation exchange polymer (e.g., sold by DuPont under the trademark Nafion) can be used with a non-volatile solvent to provide a solid polymer-based electrolyte system suitable for use with electrochemical sensors. Normally conductivity is very dependent on water content and often approaches-zero in the air-dry state, but with a non-volatile solvent, adequate conductivity does not require water.

An ionically conducting solution (an electrolyte) is a salt solution; in order for salts to readily dissolve and ionize in a solvent, the solvent should have a high dielectric constant. With only a small number of exceptions, solvents with high dielectric constants are also extremely water soluble. They are generally poor solvents for polymers and not compatible with them. Identified herein are specific polymer-solvent systems with the desired combination of properties and the general classes of materials with the desired properties.

A solid polymer electrolyte system should give a plasticiser to act as a solvent for salts, a salt to provide for ionic conductivity, a polymer to make the system solid, and any necessary fabrication aids.

The basic function of the plasticizer is to act as an ionizing solvent for the salts to provide ionic conductivity and to provide the ions needed by the anode reaction or to stabilise the potential of the reference electrode. Although salts are generally insoluble in non-aqueous solvents, the plasticizer should be selected from those solvents that can be expected to have solubility for a reasonable variety of salts. This implies a high dielectric constant for the plasticizer. In addition, the plasticizer should be substantially non-volatile and not electrochemically reducible, and it should not enhance the solubility of silver chloride.

The plasticizer should swell the polymer and have sufficient compatibility so that no phase separation occurs. Although plasticizer levels as low as 30% may be acceptable, a variety of information suggests that plasticizer levels as high as 80-85% may be desirable. The plasticizer should not have any deleterious effects upon any of the materials used in the construction of the electrode.

The plasticizer will normally have a boiling point at 25° C. and 1 atmosphere pressure of at least 225° C., preferably at least 250° C. (or an equivalent lower boiling point at reduced pressure). When PVA is the polymer, the preferred plasticizer comprises an aliphatic or cycloaliphatic polyhydric alcohol having 2 to 8 carbon atoms, or mixture thereof having an average from 2 to 4 hydroxyl groups per molecule, preferably more than 2 and less than 4. Other known plasticizers for PVA, typically having hydroxy, amine or amide groups can be used.

The basic functions of the salts will vary with the nature of the sensor. For potentiometric sensors, one of the salt ions should be reversible at the reference electrode to stabilize its potential. Usually, the reference electrode is a silver/silver halide electrode in which case the anion is desirably halide ("halide"=chloride or bromide). Other types of reference electrodes are conceptually possible.

For voltammetric sensors, salts should support the anode reaction and provide adequate conductivity to prevent excessive IR drop in the electrolyte as is necessary to prevent nonlinearity. Adequate conductivity implies reasonable solubility and ionic mobility. Solubility should not be obtained by sacrificing ionic conductivity. The plasticizer should be selected to have a dielectric constant high enough to prevent excessive ion-pair formations at a selected suitable salt concentration. The halide concentration should be held to a minimum, in order to limit silver transport in voltammetric sensors. The bulk of the conductivity can be provided by an indifferent salt which does not participate in any of the electrode reactions. The salt should not react at the cathode or accelerate any degradation reactions. The salt should not enhance the solubility of the silver halide used as the reference electrode.

The basic function of the polymer is to provide a solid matrix for the plasticizer electrolyte system. The polymer should be compatible with the plasticizer at levels high enough so that a continuous plasticizer phase exists within the film. The polymer should impart enough strength so that the film will withstand the handling needed to manufacture and store the device. The polymer should have adequate long term stability. and it should not interfere with any of the electrode reactions. It should have adequate purity and not increase the solubility of the silver halide. The polymer-plasticiser-salt system should have adequate conductivity.

In general, when the polymer is plasticized it should be one which is readily solvatable by a plasticizer and have a pronounced tendency to hydrogen bond formation. These preferred characteristics can be expressed with reference to a solubility parameter and to either or both of two hydrogen bonding parameters known as Crowley's parameter $\gamma_c$ and Hansen's parameter $\delta_H$. These three parameters are to be found in the CRC Handbook of Solubility Parameters, CRC Press 1983. Table 5 on pages 153–158 and Tables 14 and 15 on pages 186–190. The solubility parameter of the polymer is preferably 24 or more, most preferably 27 or more (the value of triethylene glycol is 27.5) and still better at least 30, the units being megaPascals$^{\frac{1}{2}}$. (The value for PVC is only 19). As to H-bonding parameters, pH is preferably greater than 17 (triethylene glycol=18) and $\gamma_c$ is preferably greater than 18. Although values for the most preferred polymer, polyvinyl alcohol (hydrolyzed polyvinyl acetate), are not given in this book, triethylene glycol provides a useful marker, indicating that the values for PVA would be higher. Preferably the plasticizer and polymer have about the same solubility and hydrogen-bonding parameters. Other polymers conforming to these preferred requirements are polyvinylidene chloride and, polyacrylonitrile and various copolymers of the monomers of any of these polymers with minor amounts of appropriate co-monomers, especially vinyl chloride-hydrolyzed vinyl acetate copolymers.

A surfactant may be necessary, because it is highly desirable to continue to use Teflon as a membrane material. In general, it is desirable to use a non-ionic surfactant to avoid compatibility problems with salts. The surfactant should be compatible with both the plasticizer and the polymer. Depending on the film formation process used, other additives, such as stabilizers and internal lubricants may be necessary.

A solid polymer electrolyte can be prepared by combining, in any order, a polymer, a non-volatile solvent (plasticizer), a salt, and processing aids, such as surfactant, antioxidant, or lubricant. This is rendered into a homogeneous mixture by heat and/or with the aid of a volatile solvent. This homogeneous mixture is converted to a thin, solid, electrolyte film and adhered to a gas-permeable, water-impermeable membrane by various methods, detailed below.

A thin solid polymer electrolyte film may be made by extrusion or by casting followed by evaporation of the volatile solvent. This thin solid polymer electrolyte film may be affixed to the membrane by laminating or roll-bonding, for combining two or more polymeric materials into a single thin film. Discs of this combination material may then be incorporated into fixation rings.

The thickness of the solid electrolyte depends on the intended use. For a transcutaneous sensor, it is desirably less than 25 micrometers. For other sensors, it can be somewhat greater, although the transient response (the time taken for the device to equilibrate to 90% of its total change) is approximately proportional to the square of the thickness, so 50 or perhaps 75 micrometers would be a normal upper limit of thickness.

Alternatively, a disc of this solid polymer electrolyte film may be cut and then affixed to a selectively permeable membrane which is then incorporated into a fixation ring, or the disk may be applied to the membrane which has previously been assembled into a fixation ring.

Alternatively, the homogeneous mixture can be applied directly to the permeable membrane material by casting, transfer printing, extrusion, calendering, or other surface coating operation followed by solvent evaporation or cooling to solidify the polymer electrolyte. This permeable membrane-electrolyte combination can then be incorporated into the fixation ring assembly. In the preferred embodiment, the homogeneous mixture is applied by casting or printing to limited areas of the selectively permeable membrane, which have been previously assembled into fixation rings.

A fixation ring suitable for use with a solid electrolyte as described herein is disclosed in U.S. Pat. No. 4,280,505 to Dali et al. which is assigned to the assignee of this patent. The structure of an electrochemical transcutaneous sensor which includes a solid phase electrolyte is described briefly below with reference to FIG. 1. The structural elements of the sensor, other than the electrolyte are more fully described in U.S. Pat. No. 4,280,505 which is, herein, incorporated by reference.

Figure 1:
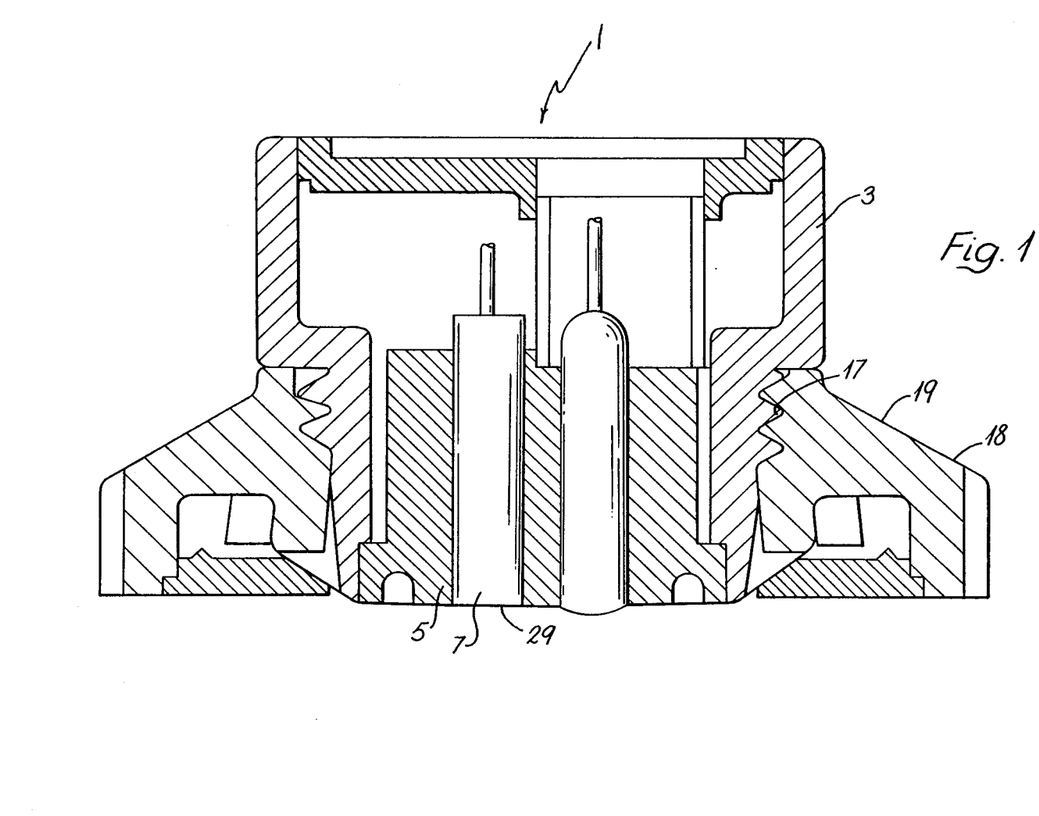
FIG. 1 is a sectional elevation view illustrating an electrochemical sensor according to a preferred embodiment of the invention.

Referring now to FIG. 1, there is shown a transcutaneous gas sensor probe 1 including a housing 3 in which there is mounted an anode 5 and a cathode 7. The housing 3 has an enlarged cylindrical upper portion and a smaller diameter lower portion with threads 17 on its exterior. A fixation ring 18 has a housing 19 with interior threads for mounting the fixation ring 18 on the housing 3. Membrane 29 is mounted on the fixation ring 18 as described therein. The membrane 29 may be formed from a material which is permeable to a gas intended to be measured, e.g., polypropylene for oxygen and teflon for carbon dioxide, with the solid electrolyte affixed to its upper surface as herein set forth. The membrane 29 may also be formed from a thin disc shaped layer of the solid electrolyte. Alternatively, the membrane 29 may comprise two or more layers, one of which is selectively permeable to the gas under study and another of which comprises a sheet of the electrolyte.

EXAMPLES

Figure 2:
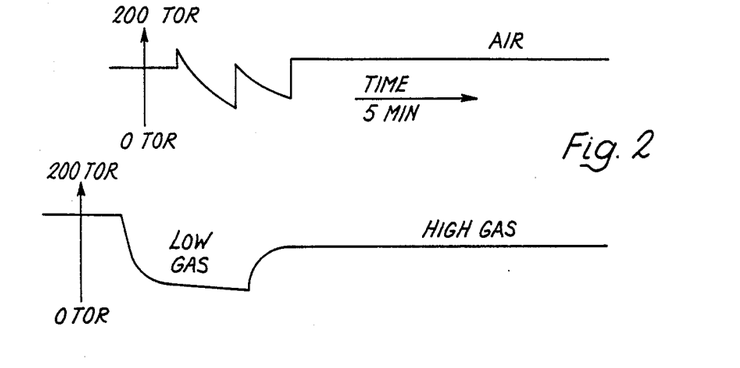
FIG. 2 is a graphic view illustrating the response of an electrochemical sensor according to one preferred embodiment of the invention.

FIG. 2 is a graphic view illustrating the response of a conventional transcutaneous oxygen electrode covered with a membrane utilizing a solid polymer electrolyte, based upon poly(vinylidene) chloride. It shows the initial rapid downward drift in air and the substantial stabilization in less than 10 minutes. It was then exposed to low gas (5% carbon dioxide in nitrogen) gradually stabilized to a reading near zero, and then showed an appropriate response to high gas (10% carbon dioxide, 12% oxygen, balance nitrogen).

Figure 3:
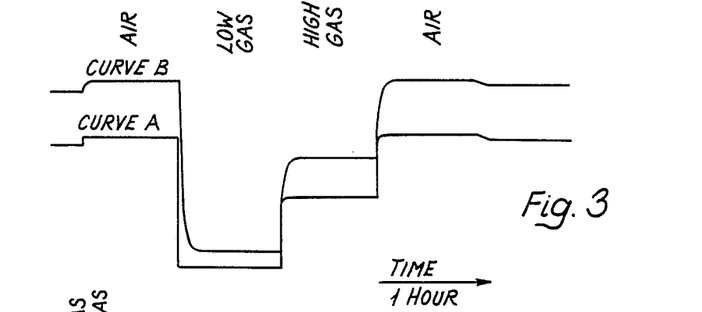
FIG. 3 is a comparative graphic view illustrating the response of an electrochemical sensor according to another preferred embodiment of the invention.

Curve B in FIG. 3 is a graphic view illustrating the response of a transcutaneous oxygen electrode having a corona-treated Teflon film coated with a solid polymer electrolyte, based upon poly(vinylalcohol) according to one example. Curve A illustrates the response of a similar electrode utilizing a conventional liquid electrolyte.

Examples of suitable polymers for a solid electrolyte system include polyethylene oxide-magnesium chloride complex, polyethylene oxide-lithium salt complexes, poly(ethylene succinate)-lithium perchlorate, -lithium thiocyanate, or -lithium fluoroborate complex, and poly(2-methoxyethyl, polyethylene glycol)methacrylate-alkali metal salt complexes, poly(perfluoroethylene sulfonic acid) and poly(perfluoroethylene carboxylic acid).

Plasticizers may include propylene carbonate, ethylene carbonate, polyethylene glycol, glycerol, 2-ethyl-2-(hydroxymethyl)-1,3-propanediol, 2-ethyl-1,3-hexanediol, 1,2,6-hexanetriol, 2,2-diethyl-1,3-propanediol, 1,1,1-tris(hydroxymethyl)ethane, gamma-butyrolactone, 1,3-cyclohexanediol, and 1,4-cyclohex-anedimethanol.

Salts may include lithium nitrate, lithium chloride, magnesium nitrate, magnesium chloride, tetrabutylammonium nitrate, tetrabutyl ammonium bromide, tetrabutylammonium chloride, tetraetheylammonium nitrate, tetraethylammonium perchlorate, tetraethylammonium chloride, tetraethylammonium bromide, potassium nitrate, and potassium acetate.

Surfactants may include DuPont Zonyl surfactants FSP, and FSN, and 3M Fluorad Surfactants FC-170-C and FC-93.

The manufacturer's data define these surfactants as follows. DuPont FSN is $F(CF_2CF_2)_{3-8}CH_2CH_2O)H$. DuPont FSP is $(F(CF_2CF_2)_{3-8}(CH_2CH_2O)_{1,2}P(O)-(ONH4)_{2,1}$. 3M FC-93 is ammonium perfluoralkyl sulfonates and 3M FC-170-C is fluorinated alkyl polyoxyethylene ethanols.

A. GELLED ELECTROLYTE SYSTEM

To 100 ml of a 95% ethylene glycol-water mixture at or below room temperature, add gradually, with good stirring, 0.75 g of Viscarin, a Kappa-II carrageenan provided by the Marine Colloids Div., FMC Corporation, Springfield, NJ 07081. When this is thoroughly dispersed, warm it on a hot water bath, with stirring, until it is a uniform solution. Continue heating until it is 75 degrees C., transfer to a blender, add 2.55 g $NaNO_3$ and 1.0 ml 1.0M NaCl solution and blend until it appears homogeneous. Reheat to 75 degrees C., add 1.0 ml 2.56M $KHCO_3$ solution and blend again. To half this solution, add 0.15 ml Zonyl FSP 35% solution (an anionic fluorosurfactant) provided by the DuPont Corp., Wilmington, Delaware. Blend until homogeneous. Maintain at 75-80 degrees C. without stirring until the solution is homogeneous. While the solution is at the above specified temperature, centrifuge in a clinical centrifuge until it is clear and free of all bubbles. Upon cooling to room temperature, this material sets to a soft gel.

This carrageenan-based gel melts at 40-60 degrees C., so that very small drops can be dispensed onto the interior surface of a membrane mounted in a NovaDisk membrane attachment device used for a transcutaneous electrode. When the fluid has cooled to room temperature, it gels again and can be handled and shipped without any flow. When applied to the surface of an electrode at operating temperature, it flows well enough to form a thin film, providing normal operation.

Samples of these membranes were clinically tested with satisfactory results.

There is no need to limit the solvents to those that have historically been used in gas sensing electrodes. Solvents less volatile than ethylene glycol and water can be used if their diffusional properties are acceptable. This greatly expands the number of potential gelling agents because they do not have to be water soluble. Although not gelled, a system utilizing a mixture of propylene carbonate and polyethylene glycol 1000 showed excellent transient response and sensitivity.

Other polymers that are suitable for gelling the wide range of plasticizers that are potential candidates as non-volatile electrolyte solvents include materials such as polyacrylamide and modified celluloses, such as sodium carboxymethyl-cellulose, hydroxypropylcellulose, etc. There are well known methods to crosslink and, therefore, gell, all of these polymers.

B. POLYMER-PLASTICISER SYSTEM

Example 1

Saran F278, a proprietary co-polymer, predominantly poly(vinylidene chloride) (Dow Chemical Co., Midland, MI), 2.038 gm and propylene carbonate 2.071 gm were added to 3.012 gm tetrahydrofuran (THF) and 1.494 gm xylene and dissolved at 65° C. To half this solution, 16 mg of tetraethylammonium chloride was added; this yielded a clear solution. This was cast on to a glass plate and dried at 65° C. The resistance measured with an AC conductivity bridge, was 500,000 to 1,000,000 ohms.

A 0.25 inch (6.3 mm.) diameter circle was cut from this material. It was mounted on the face of a transcutaneous oxygen sensor covered with a standard Nova-Disk membrane attachment device. The sensor responded to oxygen.

Example 2

Saran F310, a proprietary co-polymer, predominantly poly(vinylidene chlorides (Dow Chemical Co., Midland, MI) 1.584 gm and 2.418 gm propylene carbonate solution which is 0.3M in tetraethylammonium perchlorate and 0.01M in tetraethylammonium chloride were added to 6.590 gm methylethylketone. After warming at 65° C. for two hours with ultrasonic agitation, this yielded a homogeneous, more or less clear solution. This was cast onto glass and dried at 65° C. for one hour. This produced a clear, tough, highly stretchable film.

A sample of this solution was cast onto a corona-treated Teflon film and mounted on a transcutaneous oxygen electrode.

Example 3

Poly(vinylidene fluoride) CAT #102 (Scientific Polymer Products, Inc., 6265 Dean Parkway, Ontario, NY 14519) 1.789 gm and 2.435 gm of a propylene carbonate solution which is 0.3M in tetraethylammonium perchlorate and 0.01M in tetraethylammonium chloride, were added to 6.727 gm of cyclohexanone. After warming at 65° C. for two hours with ultrasonic agitation, the polymer had not completely dissolved, so the mixture was placed in a boiling water bath at 100° C. It slowly dissolved, yielding a highly viscous solution, which gelled on cooling to room temperature overnight. The solution was diluted by adding 2.018 gm of cyclohexanone and heated on the boiling water bath until it was homogeneous. The polymer solution at 100° C. was cast on to a glass plate at 65° C. After drying at 65° C. for 1.5 hours, a cloudy film was obtained which gave a high response upon loose application to the face of a transcutaneous oxygen electrode.

Example 4

Poly(acrylonitrile) (PAN) Cat #134, nominal M.W. 150,000, was obtained from Scientific Polymer Products, Inc., 6265 Dean Parkway, Ontario, NY. A solution was prepared by taking 5.0 ml of a 9.5% solution of PAN in dimethylformamide (DMF), and adding 2.415 gm of a propylene carbonate solution 0.3M in tetraethylammonium perchlorate and 0.01M In tetraethylammonium chloride. The mixture was heated at 75°-85° C. until it was a homogeneous solution. This material, cast on glass and dried at 65° C., yielded a plasticized film. When placed on a transcutaneous oxygen electrode, a response of 1.77 pA/Torr was obtained.

Example 5

Figure 4:
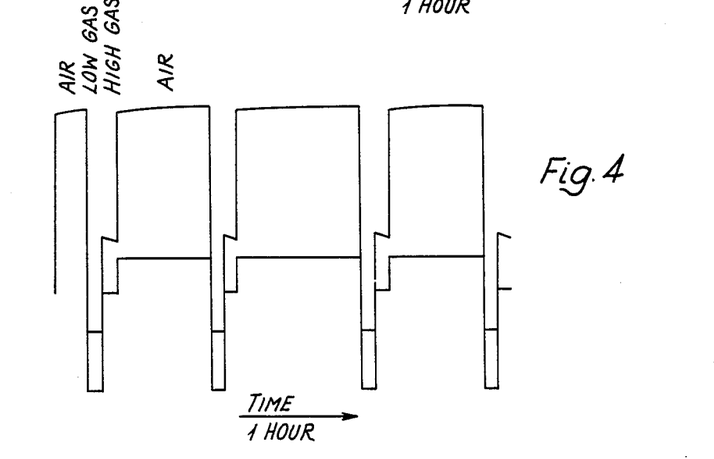
FIG. 4 is another comparative graphic view illustrating the response of an electrochemical sensor according to another preferred embodiment of the invention.
Figure 5:
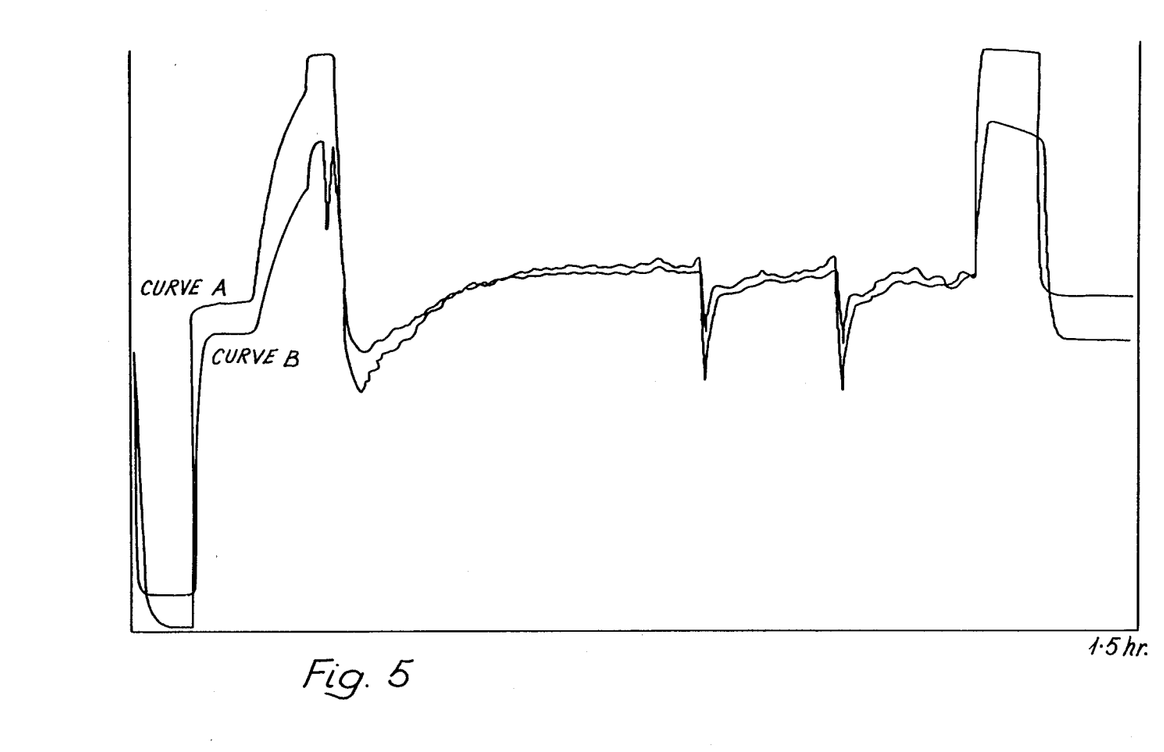
FIG. 5 is a comparative graphic view further illustrating the response of an electrochemical sensor in its intended environment.

Poly(vinyl alcohol) (PVA) Cat #334, MW 125,000, 88% hydrolysed was obtained from Scientific Polymer Products, Inc., 6265 Dean Parkway, Ontario, NY. A 7.44% solution of polymer in water was used to prepare a variety of films. For example, 2.69 ml of this solution was taken. To it, the following plasticizer solutions were added: 1.2 ml of a 25% solution of trimethylol propane in water and 1.2 ml of a 25% solution of glycerol in water. For salts, there were added 0.6 ml of 1.0M tetrabutyl ammonium nitrate (TBNO$_3$) end 0.6 ml of 0.1M tetrabutyl ammonium chloride (TBACl). To promote better casting, 0.1 ml of a 2% solution of DuPont FSN surfactant was added. This solution was heated to ensure uniformity and then cast on the inner surface of a NovaDisk membrane attachment device containing a Teflon membrane. After drying at 65° C. for 1.0 hours, this was applied to a transcutaneous oxygen electrode. FIG. 4 shows the initial 15 hours of the response of this electrode with various gases on a calibration device during a laboratory test, to air, low gas, high gas, and back into air. Curve A shows a conventional electrode utilizing a liquid electrolyte, and Curve B shows a similar electrode with a solid polymer electrolyte, based upon poly(vinylalcohol). FIG. 5 shows the response of another electrode with a different solid polymer electrolyte upon application of the sensor to the skin of a volunteer. Curve A is a control utilizing a conventional liquid electrolyte, and Curve B is an electrode with a solid polymer electrolyte.

A variety of other materials have demonstrated utility as plasticisers. These include propylene carbonate, 2-ethyl-2-(hydroxymethyl)-1,3-propanediol, 2-ethyl-1,3-hexanediol, and several others.

From the foregoing examples, it can be concluded that many aliphatic substances with molecular weights less than two hundred, and/or having 2 to 8 carbon atoms, bearing two or more hydroxyl groups, but normally not more than four will show suitably low volatility and compatibility with these and other suitable polymers. It is not even necessary for these materials to be liquid at room temperature. One of the examples given above, 2-ethyl-2-(hydroxymethyl)-1,3-propanediol, is a solid at room temperature. These substances may also include in their structure ester groups (as in propylene carbonate) and/or ether groups (as in triethylene glycol). Compounds containing these structures have the high dielectric constants and polarity necessary to solvate and, therefore, dissolve and ionize salts.

In addition to the poly(vinyl alcohol) described above, various other grades of that polymer have shown utility. These include materials with molecular weights down to 25,000 or even to 5,000 and with polyvinyl acetate hydrolysis levels ranging from 75% to 99%. These limits are not specified as being inclusive but merely represent the limits of materials that were readily available for testing.

Various other film-forming polymers have the chemical properties needed to produce solid polymer electrolytes. These include various cellulose derivatives, such as sodium carboxymethylcellulose and hydroxypropylcellulose, polyacrylamide, poly(hydroxyethyl methacrylate), etc. Both of the cellulose derivatives are known to be plasticized by one or more of the plasticizers listed above.

A variety of salts have demonstrated satisfactory results. These include magnesium nitrate and chloride, potassium acetate, sodium bicarbonate, chloride, and nitrate, tetrabutylammonium chloride and nitrate, and tetraathylammonium chloride, nitrate and perchlorate. From this, it can be concluded that any salt soluble in the plasticizer may give satisfactory results.

It is also possible to cross-link the polymer by various chemical reactions; this is one advantage that PVA has over other polymers. It can be cross-linked by several different chemical reactions. The simplest of these is the addition of borate ion, and this has been done.

Example 6

A solution was made of 1.0 ml 9.6% PVA solution (88% hydrolyzed, 25,000 molecular weight). 1.2 ml of a plasticizer solution containing 12.5% glycerol and 12.5% 2,2-diethyl-1,3-propane-diol. 1.56 ml of a salt solution that was 0.238M in $Mg(NO_3)_2$, 0.0038M in $MgCl_2$, and 0.0096M in lithium borate. This solution was cast on glass, dried at 65 degrees C., and yielded a tough, highly elastic film. A small volume, about 10 microliters, was cast on the interior of a NovaDisk membrane attachment device membrane, dried at 65° C., and applied to a transcutaneous oxygen electrode. It gave a response of 2.5 to 3.2 pA/Torr in air.

It has recently been shown that the helical structure of polyethylene oxide will complex alkali metal ions, producing salt-polymer complexes with relatively high conductivity. These materials, particularly if plasticized with compatible low molecular weight materials, show sufficient electrical conductivity and gas permeability to function as an electrolyte in electrochemical sensors. Specifically, a high molecular weight polyethylene oxide could be plasticized with any of the plasticizers disclosed above. Since most of these plasticizers will dissolve and ionize most of the salts listed above, adequate conductivity is obtainable.

A recent publication, "Solid Polymer Electrolyte Complexes of Alkali Salts with Poly(methacrylate)s Carrying Pendant Glyme Chains," Polymer Preprints, 25, no. 2, 107 (1984), describes a polymethacrylate with covalently bonded polyethylene oxide side chains which shows significant conductivity. The authors also note that the addition of propylene carbonate to the polymer leads to greatly increased conductivity. As noted above, the vapor pressure of propylene carbonate is too high for preferred use with many polymers in an electrochemical sensor, and other plasticizers of the sort described above can be expected to be equally effective and more resistant to evaporation.

Nafion is a fluorinated, sulfonic-acid, ion exchange polymer which is soluble, by proper treatment, in mixtures of water and the lower alcohols. When a film is cast from this solution and dried, it has excellent resistance to redissolving in water. It has excellent conductivity and gas permeability but only when it contains considerable water. This is also expected when it is solvated with plasticizer. Dissolution of the salts increases conductivity when this polymer is utilized in highly concentrated solutions where the total electrolyte concentration in the membrane phase can be expected to be very high.

Salts should be soluble in one or more of the above plasticizers. They should include an ion which can stabilize the reference electrode in potentiometric sensors or provide for an anode reaction in voltametric sensors. The salts should not be reducible at the cathode nor increase the solubility of the anode in voltametric sensors. The salts should provide sufficient conductivity so that the voltage drop through the electrolyte in voltametric sensors does not cause excessive nonlinearity. Salts which have been found satisfactory include lithium nitrate and chloride, magnesium nitrate and chloride, tetrabutylammonium nitrate and chloride, tetraethylammonium nitrate, perchlorate, and chloride, potassium nitrates and potassium acetate. It is reasonable to suppose that a great many other alkali and alkaline earth ions will have salts showing the requisite properties.

To prepare a solid polymer electrolyte by casting an aqueous solution onto a Teflon film, it is necessary to utilize an extremely effective surfactant. Materials that have been used include DuPont Zonyl surfactants FSP and FSN; these are both fluorosurfactants. Other preparation methods may require other processing aids.

Solid polymer electrolyte may be prepared by casting the mixture from a suitable solvent or directly from a mixture of the components by extrusion, by injection moulding, and by plastisol technology, i.e., by heating a suspension of finely divided polymer in a plasticizer solution of the salts and any needed processing aids, such as surfactants, antioxidants, etc.

It is to be appreciated that variations and modifications may be made to the preferred embodiments of the invention disclosed herein without departing from the spirit and scope of the invention.

I claim:

1. An electrochemical sensor comprising an electrolyte and an analyte separated by a selectively permeable membrane where the electrolyte comprises an electrically conductive solid comprising a homogeneous dispersion of a polymeric matrix phase, where the polymeric matrix phase is plasticized, and an electrically conductive salt said dispersion being substantially free of water, the plasticizer forming a continuous phase in which the conductive salt is dissolved.

2. A sensor according to claim 1 where the polymetric phase is a polyvinyl alcohol.

3. A sensor according to claim 2 where the polymetric phase is a hydrolyzed polyvinyl acetate having a degree of hydrolysis of from 80 to 99% and a molecular weight of at least 5,000.

4. A sensor according to claim 3 where the plasticizer comprises an aliphatic or cycloaliphatic polyhydric alcohol having from 2 to 9 carbon atoms or a mixture of the least two alcohols having an average of from 2 to 3 hydroxy groups.

5. A sensor according to claim 3 where the plasticizer comprises a mixture of glycerol with 2-ethyl-2-(hydroxymethyl)-1,3-propanediol or 2,2-diethyl-1,3-propanediol.

6. A sensor according to claim 2 where the plasticizer comprises an aliphatic or cycloaliphatic polyhydric alcohol having from 2 to 8 carbon atoms or a mixture of at least two alcohols having an average of from 2 to 3 hydroxy groups.

7. A sensor according to claim 2 where the plasticizer comprises a mixture of glycerol with 2-ethyl-2-(hydroxymethyl)-1,3-propanediol or 2,2-diethyl-1,3-propanediol.

8. A sensor according to claim 1 where the polymetric phase has a solubility parameter of at least 24 megaPascalsq, and a hydrogen bonding parameter $\gamma_c$ (Crowley) greater than 18 or $\delta_H$ (Hansen) greater than 17.

9. A sensor according to claim 8 where the plasticizer has about the same solubility parameter and hydrogen bonding parameter as the polymetric phase.

10. A sensor according to claim 9 where the plasticizer has a boiling point of at least 225° C. at 25° C. and 1 atmosphere.

11. A sensor according to claim 9 where the boiling point is at least 250°.

12. A sensor according to claim 8 where the plasticizer has a boiling point of at least 225° C. at 25° C. and 1 atmosphere.

13. A sensor according to claim 8 where the boiling point is at least 250°.

14. A sensor according to any one of claims 1 and 3-11 and 4-11 where the electrolyte has a thickness not greater than 25 micrometers.

* * * * *

UNITED STATES PATENT AND TRADEMARK OFFICE
CERTIFICATE OF CORRECTION

PATENT NO. : 4,925,544

DATED : May 15, 1990

INVENTOR(S) : Goldring

It is certified that error appears in the above-identified patent and that said Letters Patent is hereby corrected as shown below:

At column 1, line 34, change "sensor" to --sensors--.

At column 3, line 47, after "plasticizer" insert --)--.

At column 4, lines 38-39, change "characterstc" to --characteristic--.

At column 6, line 31, after "and" insert --fluoride-- .

At column 8, line 22, change $F(CF_2CF_2)_{3-8}CH_2CH_2O)H$ to --$F(CF_2CF_2)_{3-8}CH_2CH_2O(CH_2CH_2O)H$--.

At column 14, claim 14, first and second lines, change "1 and 3-11 and 4-11" to --1-13--.

Signed and Sealed this

Fifteenth Day of October, 1991

*Attest:*

HARRY F. MANBECK, JR.

*Attesting Officer*    *Commissioner of Patents and Trademarks*